United States Patent
Kobuke et al.

[11] Patent Number: 5,463,099
[45] Date of Patent: Oct. 31, 1995

[54] EXTRACTANT FOR SELECTIVELY EXTRACTING STRONTIUM FROM AQUEOUS SOLUTION CONTAINING THE SAME

[75] Inventors: Yoshiaki Kobuke, Hamamatsu; Akio Togashi, Tsuchiura; Masaki Ozawa; Masayuki Watanabe, both of Ibaraki, all of Japan

[73] Assignee: Doryokuro Kakunenryo Kaihatsu Jigyodan, Tokyo, Japan

[21] Appl. No.: 392,511

[22] Filed: Feb. 23, 1995

[30] Foreign Application Priority Data

Mar. 11, 1994 [JP] Japan .................................... 6-040231

[51] Int. Cl.⁶ .................................. C07F 1/08; C07F 3/06; C07F 15/04
[52] U.S. Cl. ............................ 556/117; 556/130; 556/146; 423/155; 252/182.12; 534/15
[58] Field of Search ........................... 556/117, 130, 556/146; 252/182.12; 534/15

[56] References Cited

U.S. PATENT DOCUMENTS 3,745,187  7/1973  Noguchi et al. ............. 260/455 A
3,769,308  10/1973 Kohmoto et al. ............. 260/438.1
3,772,354  11/1973 Fedricks et al. ............. 260/429 J

*Primary Examiner*—Porfirio Nazario-Gonzales
*Attorney, Agent, or Firm*—Wenderoth, Lind & Ponack

[57] ABSTRACT

An extractant for selectively extracting strontium from an aqueous solution containing the same, which comprises a 1,2-benzenebis(1,4-dioxanonyl-6,8-dionato)metal complex of the following structural formula:

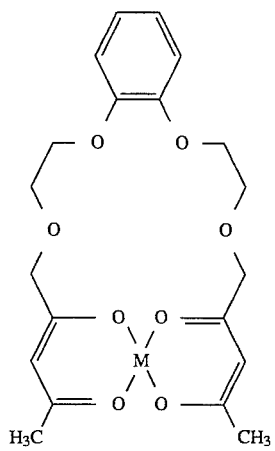

wherein M represents a metal ion of Cu (II), Zn (II) or Ni (II).

3 Claims, 2 Drawing Sheets

EXTRACTANT FOR SELECTIVELY EXTRACTING STRONTIUM FROM AQUEOUS SOLUTION CONTAINING THE SAME

BACKGROUND OF THE INVENTION

The present invention relates to an extractant effective in selectively extracting and removing strontium (Sr) from an aqueous solution containing the same.

A high-level radioactive liquid waste generated in the step of reprocessing a spent nuclear fuel contains radioactive isotopes which have long half-lives or an exothermic property, thereby posing problems in the processing and disposal of the liquid waste. It is demanded to selectively remove Sr, which is particularly an exothermic nuclide having a long half-life among the radioactive isotopes.

Investigations have been made hitherto on solvents capable of selectively extracting a metal ion from an aqueous solution containing the same. Among them, for example, an extractant having a capability of causing structure-function transformation is known. As shown in FIG. 2, this extractant can, merely by constituting it as a linear chain compound having neutral ligands (N) and, in addition, anionic ligands (A) at its terminals, induce a structural change by utilizing the coordination of the anionic ligands to the first transition metal ($M_1$) to change its structure from the linear one to a cyclic one, thereby creating a new molecular arrangement for accepting the second metal ion ($M_2$) in cooperation with the neutral ligands.

Therefore, the extractant having the capability of causing structure-function transformation has features such that it can be synthesized more easily than the conventional cyclic compounds such as crown ethers, that it can capture various metal ions, since both electronical and conformational nature of the site can be changed by changing $M_1$, and that it can control the incorporation and release of $M_1$ by the oxidation and reduction of $M_1$ itself, thus facilitating the capture and release of $M_2$.

However, among the extractants having the above-described capability, no extractant particularly effective in selectively extracting Sr has been synthesized hitherto.

SUMMARY OF THE INVENTION

The present invention has been completed after investigations made for the purpose of solving the above-described problems. An object of the present invention is therefore to provide an extractant having a selectivity toward Sr separation in an aqueous solution, so as to remove Sr which is a nuclide having a long half-life and an exothermic property, from a high-level radioactive liquid waste.

Namely, the extractant of the present invention for selectively extracting Sr from an aqueous solution containing the same comprises a 1,2-benzenebis(1,4-dioxanonyl-6,8-dionato)metal complex of the following structural formula:

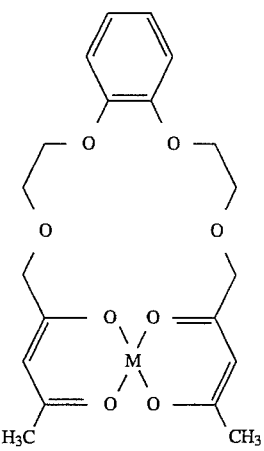

wherein M represents a metal ion of Cu (II), Zn (II) or Ni (II).

Before the incorporation of M, this compound has a linear structure having a β-diketone structure at the terminals thereof as an anionic ligand fields and then form a complex with the metal M to form a pore serving as a Sr-capturing space.

PREFERRED EMBODIMENTS OF THE INVENTION

Figure 1:
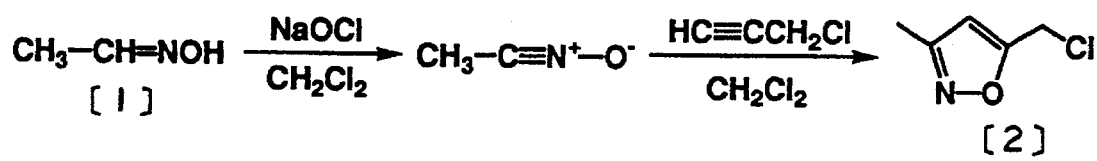
FIG. 1 is a reaction scheme of synthesis showing an example of the synthesis of the extractant of the present invention.
Figure 1:
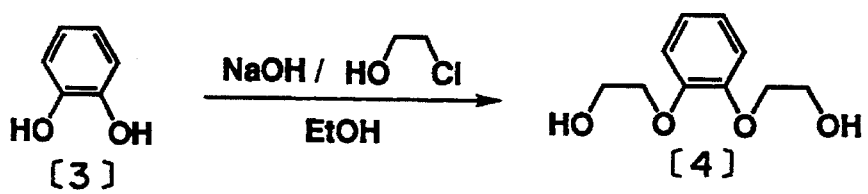
Figure 1:
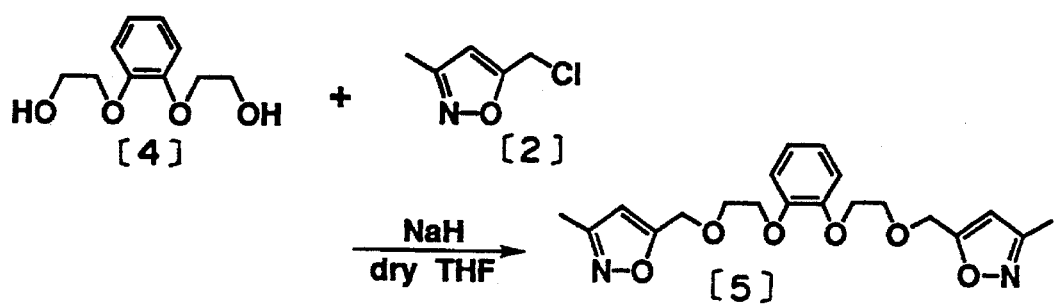
Figure 1:
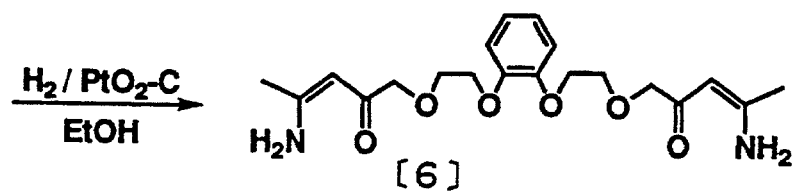
Figure 1:
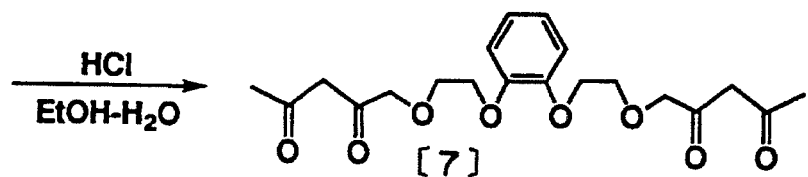
Figure 1:
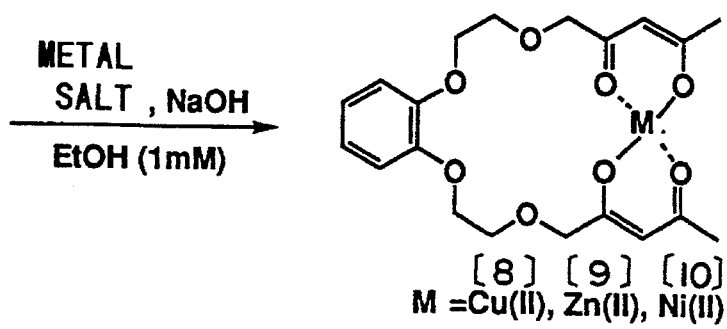
Figure 2:
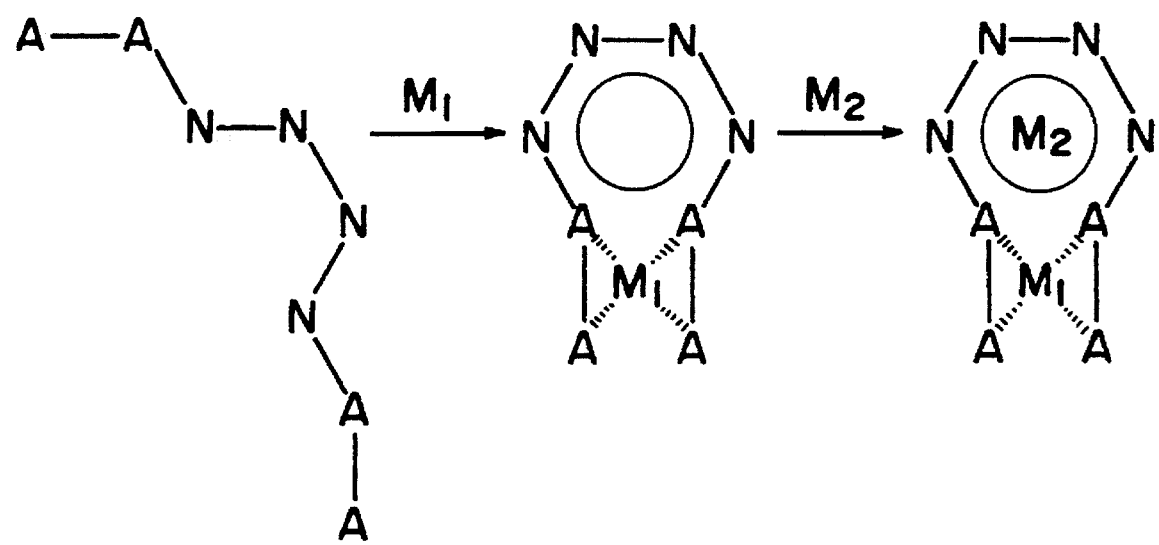
FIG. 2 is an explanatory drawing showing the general principle of the compound having a capability of causing structure-function transformation.

The following Synthesis Examples will further illustrate the synthesis of the extractants of the present invention with reference to the reaction scheme of synthesis as shown in FIG. 1. The numeral found in the brackets after each compound corresponds to the number assigned to the structural formula of that compound in FIG. 1.

Synthesis of acetaldoxime [1]

An aqueous solution (75 ml) of sodium hydroxide (63.75 g, 1.59 mol) was slowly added to an aqueous solution (75 ml) of hydroxylamine hydrochloride (81.25 g, 1.17 mol) in an ice bath. Acetaldehyde (50.00 g, 1.14 mol) and water (25 g) were slowly dropped into the resultant mixture in 1.5 hours. After stirring for 15 hours, sodium chloride was added to the obtained mixture to saturation. The formed aqueous layer was extracted with ether (8×600 ml). The combined ether layers were dried (over $CaCl_2$), and then ether was distilled off under reduced pressure. Acetaldoxime [1] was distilled (at 112° to 114° C.) from tile residue.

Synthesis of 5-chloromethyl-3-methylisoxazole [2]

Acetaldoxime [1] (14.66 g, 0.253 mol) and propargyl chloride (18.81 g, 0.253 mol) were dissolved in methylene chloride (300 ml), and the solution was immersed in an ice bath. A 5% aqueous sodium hypochlorite solution (432.26 g, NaOCl 0.290 mol) was dropped into the solution in 1 hour. After stirring under cooling in an ice bath for 1 hour, the methylene chloride layer was separated, and the aqueous layer was extracted with methylene chloride (3×150 ml). The combined methylene chloride layers were dried (over $MgSO_4$) and then methylene chloride was distilled off under reduced pressure. Compound [2] was distilled from the residue under reduced pressure (0.35 mmHg, 39° C.).

TLC: Rf=0.5 (benzene) NMR (60 MHz): $\delta 2.21$ (s, 3.2H, a) $\delta 4.50$ (s, 2.0H, b) $\delta 6.11$ (s, 1.0H, c)

Synthesis of 1,2-bis(2-hydroxyethoxy)benzene [4]

Pyrocatechol [3] (55.0 g, 0.50 mol) was added to a solution (500 mol) of sodium hydroxide (50.5 g, 1.26 mol) in ethanol under purging with nitrogen, and the resultant mixture was refluxed under stirring with a mechanical stirrer for 30 minutes. Ethylene chlorohydrin (96.5 g, 1.20 mol) was dropped into the mixture in 1 hour. After refluxing overnight, the reaction was judged to have been completed. Ethanol was distilled off and chloroform (1.5 l) was added to the residue. The chloroform layer was extracted with an aqueous NaOH solution while the removal of an unreacted matter was confirmed by UV spectroscopy (seven times each with 20 ml of the aqueous NaOH solution for 500 ml of the chloroform layer until no change had been observed in the absorption at around 275 nm in the UV spectrum even when the alkaline aqueous layer turned acidic after the completion of the extraction). Chloroform was distilled off under reduced pressure to obtain the compound [4].

TLC: Rf=0.41 (EtOAc) NMR (60 MHz): $\delta 3.79$–3.89 (m, 9.8H, a+b) $\delta 6.80$ (s, 4.0H, c) UV: $\lambda_{max}$=275 nm ($H_2O$) m.p.: 77°–80° C.

Synthesis of 1,2-bis(2-(3-methyl-5-isoxazolyl)-methoxyethoxy)benzene [5]

Sodium hydride (0.73 g (55%), 16.7 mmol) dispersed in oil was added to a solution of the compound [4] (1.50 g, 7.57 mmol) in dry THF (50 ml). After refluxing for 1 hour, a solution of the compound [2] (2.20 g, 16.7 mmol) in dry THF (15 ml) was dropped into the resultant mixture under reflux for 30 minutes. After refluxing for additional 8 hours, the disappearance of the compound [4] and the formation of the compound [5] were confirmed by TLC, thus judging the reaction to have been completed. THF was distilled off, and a saturated aqueous sodium chloride solution (10 ml) and ether (30 ml) were added to the residue. The ether layer was separated, and the aqueous layer was extracted with ether (5×30 ml). The combined ether layers were dried (over $Na_2SO_4$) and ether was distilled off under reduced pressure to obtain a crude product, which was then recrystallized (from ether/n-hexane) to obtain a colorless solid [5].

TLC: Rf=0.41 (benzene: EtOAc=5:2) NMR (60 MHz): $\delta 2.18$ (s, 6.0H, a) $\delta 3.90$ (s, 7.8H, b) $\delta 4.54$ (s, 4.0H, c) $\delta 5.97$ (s, 2.0H, d) $\delta 6.78$ (s, 4.0H, e) UV: $\lambda_{max}$=235.1 nm, 276.9 nm MS: 388 ($M^+$)

Synthesis of 1,2-bis(8-amino-1,4-dioxa-6-oxo-7-nonenyl)benzene [6]

Platinum dioxide (0.08 g) and activated carbon (0.40 g) were added to ethanol (30 mol), followed by purging with hydrogen and stirring at room temperature for 30 minutes. The compound [5] (2.45 g, 6.31 mmol) was added to the mixture, followed by stirring at room temperature in a hydrogen atmosphere. The reaction was judged to have been completed after 5 hours, since the conversion of the compound [5] ($\lambda_{max}$: 235.1 nm, 276.9 nm) into the compound [6] ($\lambda_{max}$: 232.4 nm, 303.8 nm) was confirmed by UV spectroscopy, and the disappearance of the compound [5] and formation of the compound [6] were confirmed by TLC. The precipitate was separated by filtration and ethanol was distilled off under reduced pressure to obtain the compound [6]. The compound [6] can be purified by column chromatography ($CHCl_3$: MeOH=10:1).

TLC: Rf=0.54 (EtOAc: MeOH=4:1) Rf=0.42 ($CHCl_3$: MeOH=10:1) NMR (60 MHz): $\delta 1.80$ (s, 6.0H, a) $\delta 3.65$–4.09 (m, 12.7H, b+c) $\delta 5.11$ (s, 1.8H, d) $\delta 6.80$ (s, 4.0H, e) UV: $\lambda_{max}$=232.4 nm, 303.8 nm Synthesis of 1,2-bis(1,4-dioxa-6,8-dioxononyl)benzene [7]

Water (10 ml) and 12N hydrochloric acid (5 ml) were added to ethanol (100 ml), and then the compound [6] (2.47 g, 6.29 mmol) was added to the resultant mixture under stirring at room temperature. After stirring overnight, the conversion of the compound [6] ($\lambda_{max}$:232.4 nm, 303.8 nm) into the compound [7] ($\lambda_{max}$: 232.5 nm 275.5 nm) was confirmed by UV spectroscopy, thus judging the reaction to have been completed. The solvent was distilled off under reduced pressure and then chloroform (50 ml) and a saturated aqueous sodium chloride solution (10 ml) were added to the residue. The aqueous layer was separated, and the chloroform layer was extracted with a saturated aqueous sodium chloride solution (3×10 ml). The chloroform layer was dried (over $Na_2SO_4$) and then chloroform was distilled off under reduced pressure to obtain the compound [7].

NMR (90 MHz): $\delta 6$ 2.05, 2.21 (s, 5.2H, a+b) $\delta 6$ 3.65–4.22 (m, 12.1H, c+d+e) $\delta 6$ 5.81 (s, 0.9H, f) $\delta 6$ 6.92 (s, 4.0H, g) $\delta 6$ 15.1 (br, 0.5H, h) UV: $\lambda_{max}$=232.5 nm, 275.5 nm (EtOH)

Synthesis of 1,2-benzenebis(1,4-dioxanonyl-6,8-dionate)copper (II) [8]

An aqueous solution (in a minimum amount) of $CuSO_4.5H_2O$ (0.119 g, 0.477 mmol) was dropped into a dilute ethanol solution (210 ml: $1\times10^{-3}$M) of the compound [7] (0.188 g, 0.477 mmol) under stirring at room temperature. Then an aqueous solution (in a minimum amount) of sodium hydroxide (0.0381 g, 0.954 mmol) was dropped thereinto. The resultant mixture was stirred overnight in order to complete the formation of the complex. The reaction was judged to have been completed, since the shift of the absorption of the β-diketone part ($\lambda_{max}$: 275.5 nm) toward a longer wavelength ($\lambda_{max}$: 297.2 nm) was confirmed in the UV spectrum of the solution. The solvent was thoroughly removed by distillation under reduced pressure and vacuum drying. Chloroform was added to the residue. The precipitate was separated by filtration, and chloroform was distilled off under reduced pressure. By recrystallization of the crude product from chloroform/n- hexane, a blue solid [8] was obtained.

UV: $\lambda_{max}$=237.8 nm, 297.2 nm (EtOH) $\lambda_{max}$=252.5 nm, 301.5 nm ($CHCl_3$) m.p.: 154°–157° C. MS: 455 ($M^+$)

Synthesis of 1,2-benzenebis(1,4-dioxanonyl-6,8-dionato)zinc (II) [9]

An aqueous solution (in a minimum amount) of NaOH (16.4 mg, 0.410 mmol) was added to a dilute ethanol solution (200 ml: $1\times10^{-3}$M) of the compound [7] (80.5 mg, 0.204 mmol) under stirring at room temperature. After confirming that the compound had been completely converted into its Na salt ($\lambda_{max}$=225.7 nm, 291.0 nm) by UV spectroscopy, an aqueous solution (in a minimum amount) of $ZnSO_4.7H_2O$ (58.7 mg, 0.204 mmol) was dropped into the resultant mixture. This procedure was conducted rapidly, since the mixture would begin to get colored when it was left to stand without addition of the zinc salt. After the completion of the addition, the reaction was judged to have been completed, since the shift of the absorption of the β-diketone part ($\lambda_{max}$=275.5 nm) toward a longer wavelength ($\lambda_{max}$= 285.0 nm) was confirmed in the UV spectrum of the solution. The solvent was thoroughly removed by distillation under reduced pressure and vacuum drying. Chloroform was added to the residue. The precipitate was separated by filtration, and chloroform was distilled off under reduced pressure. By recrystallization of the crude product from chloroform/n-hexane, a colorless solid [9] was obtained.

NMR (90 MHz): δ2.00 (s, 7.0H, a) δ3.97–4.12 (m, 11.4H, b+c) δ5.21 (s, 1.1H, d) δ6.89 (s, 4.0H, e) UV: $\lambda_{max}$=231.1 nm, 285.0 nm (EtOH) MS: 479 (M+Na)$^+$ Synthesis of 1,2-benzenebis(1,4-dioxanonyl-6,8-dionato)nickel (II) [10]

An aqueous solution (in a minimum amount) of $NiCl_2 \cdot 6H_2O$ (49.2 mg, 0.207 mmol) was dropped into a dilute ethanol solution (210 ml; 1×10$^{-3}$M) of the compound [7] (81.7 mg, 0.207 mmol) under stirring at room temperature. Then an aqueous solution (in a minimum amount) of sodium hydroxide (16.6 mg, 0.415 mmol) was added to the resultant mixture. At the completion of the addition, the reaction was judged to have been completed, since the shift of the absorption of the β-diketone part ($\lambda_{max}$=275.5 nm) toward a longer wavelength ($\lambda_{max}$=297.0 nm) was observed in the UV spectrum of the solution. The solvent was thoroughly removed by distillation under reduced pressure and vacuum drying. Chloroform was added to the residue. The precipitate was separated by filtration, and chloroform was distilled off under reduced pressure. By recrystallization of the crude product from chloroform/n- hexane, a yellowish green solid [10] was obtained.

UV: $\lambda_{max}$=232.4 nm, 297.0 nm (EtOH) MS: 450 (M$^+$)

Alkaline earth metal ion extraction test 8.0 ml of a chloroform solution containing 4.0×10$^{-5}$M of the above-described compound [8] or [9] of the present invention was used as an organic phase.

0.8 ml of an aqueous solution of 1.0M of a chloride of $Mg^{2+}$, $Ca^{2+}$, $Sr^{2+}$ or $Ba^{2+}$ as a metal ion and 2.5×10$^{-4}$M of picric acid neutralized with lithium hydroxide was used as an aqueous phase.

The organic and the aqueous phases were fed into a separatory funnel, and the funnel was shaken for several minutes and then left to stand to cause phase separation. The concentration of the metal picrate ion in each phase was determined with a spectrophotometer, and the distribution ratio (amount [mol] of the picrate extracted into the organic phase/amount [mol] of the picrate remaining in the aqueous phase: index of the metal ion-extracting capacity) was calculated. The results are given in Table 1.

For comparison, dibenzo-18-crown-6 (hereinafter referred to as "DB18C6") which was a crown ether extractant of the following structural formula was used:

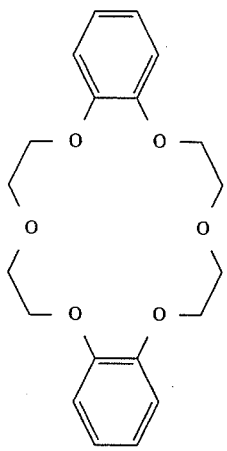

DB18C6 is the most typical compound of the crown ethers which are cyclic compounds having a pore for capturing a metal ion within it. This compound was selected as the comparative extractant, since the principle of the metal ion extraction was the same as that of the extraction with the extractant of the present invention.

Since the chlorides per se of the alkaline earth metal ions have high hydrophilic properties and exhibit a low distribution ratio, the metal salts must be converted into anions having high hydrophobic properties. Therefore, the metal salts were converted into metal picrates by adding picric acid thereto prior to the extraction test.

TABLE 1

| | Distribution ratio in metal picrate extraction | | | |
|---|---|---|---|---|
| | Metal ion | | | |
| Extractant | $Mg^{2+}$ (0.72) | $Ca^{2+}$ (1.00) | $Sr^{2+}$ (1.18) | $Ba^{2+}$ (1.35) |
| Compound [8] | 0.0413 | 2.27 | 3.32 | 1.01 |
| Compound [9] | 0.0506 | 0.947 | 1.28 | 0.711 |
| DB18C6 | — | 0.0306 | 0.0337 | 0.0198 |

(Note) The numeral found in the parentheses under each metal ion represents the ionic radius (unit: angstrom) of the metal ion.

It will be apparent from the test results given in Table 1 that the compounds [8] and [9] of the present invention each have a high distribution ratio for Sr, that this ratio is far higher than that for other metal ions, and that the effect of them are more excellent than that of DB18C6.

Further, a similar metal ion extraction test was conducted on the nickel complex of the compound [10] to find that it was also usable as the selective extractant for Sr.

As described above, the compound of the present invention is effectively usable as the extractant for selectively removing Sr from an aqueous solution containing the same.

What is claimed is:

1. A compound which is a 1,2-benzenebis(1,4-dioxanonyl-6,8-dionato)metal complex of the following structural formula:

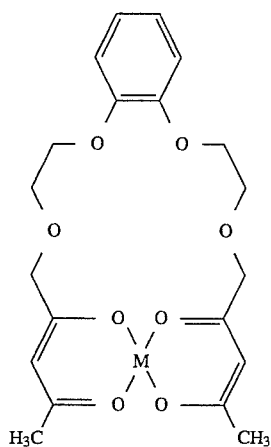

wherein M represents a metal ion of Cu (II), Zn (II) or Ni (II).

2. A composition which comprises the compound of claim 1 in an aqueous solution.

3. A method for selectively extracting strontium from an aqueous solution, comprising the steps of mixing a compound of claim 1 in an aqueous solution containing strontium to form a complex of the compound of claim 1 with strontium, and then separating the complex from the aqueous solution.

* * * * *